United States Patent
Navarro Y Koren et al.

(10) Patent No.: US 6,884,445 B2
(45) Date of Patent: Apr. 26, 2005

(54) MATRIX-FORMING COMPOSITION CONTAINING PECTIN

(75) Inventors: Peter Antonio Navarro Y Koren, Ede (NL); Katrien Maria Jozefa Van Laere, Heteren (NL); Maria Elisabeth Hermien De Lange, Wageningen (NL); Marcel Minor, Wageningen (NL)

(73) Assignee: N.V. Nutricia, MA Zoetermeer (NL)

( * ) Notice: Subject to any disclaimer, the term of this patent is extended or adjusted under 35 U.S.C. 154(b) by 386 days.

(21) Appl. No.: 10/022,372

(22) Filed: Dec. 20, 2001

(65) Prior Publication Data

US 2003/0118712 A1 Jun. 26, 2003

(51) Int. Cl.$^7$ ................................................ A23L 2/38
(52) U.S. Cl. .................... 426/72; 426/575; 426/577; 426/578
(58) Field of Search .............................. 424/439; 426/2, 426/74, 576, 578, 575, 577, 590; 514/909–911

(56) References Cited

U.S. PATENT DOCUMENTS

| | | | | |
|---|---|---|---|---|
| 4,784,861 A | * | 11/1988 | Gori | 426/74 |
| 5,068,109 A | * | 11/1991 | Foldager et al. | 424/441 |
| 5,690,981 A | * | 11/1997 | Watanabe et al. | 426/531 |
| 6,187,334 B1 | * | 2/2001 | Yamagata et al. | 424/439 |

FOREIGN PATENT DOCUMENTS

| | | |
|---|---|---|
| JP | 07-067575 | 3/1995 |
| JP | 07-069902 | 3/1995 |
| WO | WO 96/33694 | 10/1996 |

OTHER PUBLICATIONS

S. Bagheri, L. Gueguen, "Effect of wheat bran and pectin on the absorption and retention of phosphorous, calcium, magnesium and zinc by the growing pig.", Reprod. Nutr. Develop., 1985, 24 (4A), 705–716.

Translation from Japanese, Tables 11 and 12.

* cited by examiner

*Primary Examiner*—Carolyn Paden
(74) *Attorney, Agent, or Firm*—Young & Thompson

(57) ABSTRACT

One aspect of the present invention relates to a liquid edible composition with a pH of more than 6, a viscosity below 600 mPas at a shear rate of $100s^{-1}$ and 20° C., and a viscosity of at least 125% of the aforementioned viscosity at a pH below 5 and a temperature of 37° C., the composition comprising at least 0.05 wt. % of pectin having a degree of methoxylation between 2 and 50 and/or of alginate; at least 5 mg calcium per 100 ml; and at least 0.1 wt. % indigestible oligosaccharide having a degree of polymerisation between 2 and 60.

Another aspect of the invention relates to a method for the treatment or prevention of overweight or obesity in mammals, said method comprising the enteral administration to a mammal of an effective amount of the aforementioned composition.

12 Claims, No Drawings

MATRIX-FORMING COMPOSITION CONTAINING PECTIN

FIELD OF THE INVENTION

The present invention relates to a composition, which is liquid at around neutral pH and forms a viscous matrix at low pH, the composition comprising pectin, calcium and oligosaccharides. The present composition is particularly suitable for use in a method of treating or preventing overweight or obesity. Hence the present invention also encompasses a method of treating overweight or obesity in mammals, which method comprises the enteral (e.g. oral) administration of an effective amount of the aforementioned composition.

BACKGROUND OF THE INVENTION

Obesity is a major health problem with approximately ninety-seven million people considered clinically overweight in the United States.

Various chemical approaches have been proposed for controlling obesity. Anorectic agent such as dextroamphetamine, the combination of the non-amphetamine drugs phentermine and fenfluramine (Phen-Fen), and dexfenfluramine (Redux) alone, are associated with serious side effects. Indigestible materials such as olestra, mineral oil or neopentyl esters have been proposed as substitutes for dietary fat. Garcinia acid and derivatives thereof have been described as treating obesity by interfering with fatty acid synthesis. Surgical techniques such as temporary ileal bypass surgery, are employed in extreme cases.

However, methods for treating obesity, such as those described above have serious shortcomings. Controlling the diet remains the most prevalent technique for controlling obesity. Hence, new compositions suitable for the treatment of obesity are needed.

The accumulation or maintenance of body fat bears a direct relationship to caloric intake. Therefore, one of the most common methods for weight control to combat obesity is the use of relatively low-fat, high fiber diets. Especially high viscosity fibers may advantageously be employed in anti-obesity diets. The high viscosity fibers may induce a sensation of satiety when ingested in a sufficient amount.

JP2000189109 describes a food composition for the prevention and treatment of obesity having a prolonged retention time in the stomach, which is usable for the treatment of obesity and/or diabetes and which becomes gel-like at low pH. The composition includes pectin having a DE of 40% or less as a soluble fiber. The product does not include calcium or oligosaccharides.

U.S. Pat. No. 4,784,861 describes a packaged weight-control powder which can be used as a food additive to be employed before eating. Each package includes a dose to be sprinkled on the foodstuff to be eaten. The powder is formed of a mixture of oat, wheat and corn brans mixed with pectin guar gum, psyllium and cutin. Mineral supplements are employed to replace those removed by the fibers of the brans. The powder is prepared in an atmosphere of less than 50% humidity and is packed in individual water-proof packages of relatively small size.

Additionally, pectin-containing preparations are for example used as medicine carriers to provide a slow-release of bioactive agents, as antacid composition and as antiflatulent composition.

WO9633694 describes pectic preparations which comprise at least one pectin associated with a complex composition comprising firstly an effervescent pair which easily disperses the pectin in water and hydrates it and regulates the gellification process irrespective of the hardness of the water used for the suspension, and secondly a mixture of compounds which provide the calcium ions necessary for the formation of the gel in an acid medium, together with magnesium ions regulating the kinetics of the calcium availability.

WO9959542 describes a pectic preparation useful as medicine carrier, to be orally administered and capable of forming a gel in an acid medium, comprising at least a pectin having a degree of methoxylation higher than 15% and calcium ions, containing a gelling process inhibitor with a pH higher than 6. The pectic preparation does not comprise oligosaccharides.

U.S. Pat. No. 5,068,109 relates to an antacid composition with floating properties, and a method of treating or alleviating upper gastrointestinal dyspeptic disorders. The antacid composition comprises a substance a) which is soluble in water at a neutral or alkaline pH, but is capable of forming a cohesive gel at an acid pH; a substance capable of being captured in the gel structure formed by substance a) at an acid pH and one or more acid neutralizing agents capable of being trapped in the gel structure formed by substance a) at an acid pH, at least one of which causes the gel to foam when contacted with an acid. Substance a) may be a low-methoxylated pectin or an amidated pectin composition. The antacid composition lacks oligosaccharide.

SUMMARY OF THE INVENTION

The pectin containing compositions described above are not perfectly suited for the treatment of obesity or overweight, mainly because of the undesired effect on bioavailability of calcium and/or because of insufficient viscosity of the pectin matrix which is formed in the stomach at low pH. The present invention provides a solution to the above problems.

The present invention provides a composition which comprises pectin and/or alginate, calcium and oligosaccharide. The present composition is liquid (at around neutral pH) and exhibits increased viscosity at an acidic pH due to the formation of a viscous matrix.

Following ingestion, the present composition will form a viscous matrix in the stomach which induces a strong satiety effect, whilst the oligosaccharide component promotes calcium bioavailability throughout the lower gastrointestinal tract.

For the formation of a rigid matrix, low methoxylated pectin and/or alginate is required. The low methoxylated pectin and/or alginate forms a sufficiently rigid matrix when reacted with calcium to induce satiety feelings. The present inventors found that particular downsides are attached to the use of high levels of low methoxylated pectins and/or alginate in compositions for the treatment of obesity or overweight. It was found by the current inventors that compositions providing a satiety effect through the gellation of low-methoxylated pectin and/or alginate significantly reduce calcium absorption and/or bioavailability.

This finding is not in line with observations made in the relevant scientific literature. For instance, in a recent review paper, Greger et al (*Journal of Nutrition.* 1999;129:1434S–1435S) observe that investigators have observed that the addition of pectin to diets generally did not alter the absorption of most minerals, except magnesium.

This observation differs from earlier findings which were published by Bagheri et al, (1985). Bagheri et al studied the effect of low methoxylated pectin on the absorption and retention of calcium in pigs. The absorption of calcium in a diet containing high methoxylated apple pectin was about 76% compared to a control diet. When low methoxylated pectin was consumed, the absorption of calcium was reduced to about 1% compared to the control diet.

Calcium is essential in a diet. Calcium deficiency may result in the following symptoms: muscle cramps, brittle nails, eczema, aching joints, increased cholesterol levels, rheumatoid arthritis, tooth decay and numbness in the arms and/or legs. Additionally, it is of importance in compositions, which are used to prevent or treat overweight and obesity. It has been described that calcium contributes to the prevention of overweight when absorbed by the body. Consequently there are severe limitations to the use of low methoxylated pectins in compositions designed to reduce body weight and/or to prevent body weight increase due to the impact of pectin and/or alginate on the bioavailability of calcium.

The ingestion of a nutritional composition, including those that are designed to prevent or treat excessive body weight, should not become an undue burden. Humans participating in a weight control program including a specific diet (i.e. having the desire to lose body weight and pursuing that goal) often prematurely discontinue the program due to the adverse taste, insufficient palatability or difficulty of consuming the dietary components. It is the inventors experience that compositions which are to be consumed in liquid form, form less of a burden for subjects participating in a weight control program than do solid or semisolid formulations. It is therefore a prerequisite that a composition designed to reduce body weight or control the caloric intake is provided in a liquid form, with limited viscosity. However, this provides an additional challenge, since calcium and low methoxylated pectins form a viscous mass when present in an aqueous environment.

It was found by the inventors that the calcium absorption inhibitory effect of low methoxylated pectins and/or alginate present in liquid edible composition can be decreased effectively through the coadministration of indigestible oligosaccharides with a degree of polymerisation between 2 and 60 and calcium. The present liquid edible composition uses a calcium salt which provides only limited amounts of free calcium ions at around neutral pH and an increased amount of free calcium ions at acidic pH. The present composition thus provides a composition which is easy to consume, which induces feelings of satiety after ingestion and which ensures sufficient calcium bioavailability.

Without wishing to be bound by theory, the inventors believe that the oligosaccharides used in accordance with the present invention provide a readily metabolisable substrate for the intestinal flora. Ingestion of oligosaccharides will result in an increase of the mass of intestinal bacteria and/or increase the activity of these bacteria, and thereby stimulate the degradation of the pectin matrix. Through the stimulated breakdown of the pectin matrix in the small intestine and colon, the calcium bioavailability will be increased through stimulated release of the pectin bound calcium. Still the pectins will have provided the desired satiety inducing effect through the formation of a viscous matrix in the stomach and/or intestine.

Additionally, the fermentation of the oligosaccharides by the intestinal bacteria will yield short chain fatty acids (SCFA), including butyrate, propionate and acetate, resulting in a decreased pH in the colon, which increases mineral solubility, hence raises the concentration of ionized calcium and accelerates the passive diffusion of calcium. Additionally, SCFA may be responsible for a rise in caecal blood flow and consequently increase mineral absorption. Furthermore, oligosaccharides may stimulate intestinal calcium transport by hypertrophy of the caecal wall, thereby increasing the surface area where mineral exchange takes place, thus improving calcium absorption.

The present composition can be advantageously used in a method for the prevention or treatment of obesity or overweight and is especially useful for subjects, preferably humans, which participate in a weight control program (e.g. the ingestion of a particular diet with the aim to reduce body weight).

The composition according to the invention aims to provide several advantageous health effects to overweight or obese subjects:

Satiety: The composition will, after ingestion, provide a feeling of satiety and thereby reduce or eliminate the desire for further food intake. The satiety inducing effect can be at least partially be contributed to the increased viscosity of the chyme in the stomach by the action of the low methoxylated pectin and/or alginate and calcium. An important advantage of the present composition resides in the fact that the resulting satiety will not rapidly disappear as is the case with many, particularly low caloric foodstuffs.

Bioavailable calcium: Overweight subjects benefit from the intake of bioavailable calcium. However, sufficient daily intake of calcium is often not reached, for example, because obese or overweight subjects tend to consume insufficient calcium rich dairy products, and instead consume vast amounts of soft drinks. Soft drinks are generally high in phosphates, the phosphates being responsible for a further decrease in the bioavailability of calcium. Calcium stored in fat cells (intracellular calcium) causes the metabolic derangements associated with obesity. Low calcium diets increase circulatory calcitrophic hormones levels, which stimulate adipocyte calcium influx which subsequently results in an increased lipogenesis and a decreased lypolysis.

Help reduce or prevent the increase of blood serum cholesterol levels: Overweight or obese subjects often suffer from increased cholesterol levels and/or an increased risk at coronary disease. The soluble fiber present in the composition, especially pectin optionally combined with -glucan, will lower blood serum cholesterol level by binding ileal bile acid in the intestine. The soluble fibers are able to interact with bile acids which results in an increased fecal excretion of bile acids. Bile acids are derived from cholesterol, and are normally effectively recycled by reabsorption from the ileum and resecretion by the liver as bile salts. To the extent that bile acids are lost with the feces, the liver must replace the lost bile salts using cholesterol. Additionally, the viscosity and gelling properties of soluble fibers may have important effects on the hydrolysis and absorption of cholesterol and the absorption of bile acids in the small intestine.

Increase stool frequency: Oligosaccharides are known to improve bowel movement, stool output and stool frequency. This is advantageous for many subjects suffering from overweight, because many obese or overweight subjects suffer from Provides sufficient water: It is the inventors believe that individuals tend to eat a constant volume of food because stomach distension triggers afferent vagal signals of fullness. According to this hypothesis, consumption of foods with high energy density (ED) will encourage consumption of excess energy because of the small volume of food in relation to energy content. A study of Bell et al. (Am J Clin Nutr 1998; 67;412–20) demonstrates that energy density influences energy intake. Significantly more energy is consumed in the condition of high energy density than in the medium or low energy density conditions. Variations in water contents between foods have a big impact in ED because water has zero energy content.

DETAILED DESCRIPTION OF THE PREFERRED EMBODIMENTS

One aspect of the present invention relates to a liquid edible composition with a pH of more than 6, preferably a pH of 6–9, a viscosity below 600 mPas (mPa·s) at a shear rate of $100s^{-1}$ and 20° C. at around neutral pH and a viscosity of at least 125% of the aforementioned viscosity at a pH below 5 and a temperature of 37° C., the composition comprising:

a. at least 0.05 wt. % of pectin having a degree of methoxylation between 2 and 50 and/or of alginate;

b. at least 5 mg calcium per 100 ml; and c. at least 0.1 wt. % indigestible oligosaccharide having a degree of polymerisation between 2 and 60.

Another aspect of the present invention concerns a method for the treatment or prevention of overweight or obesity in mammals, said method comprising the enteral administration to a mammal of an effective amount of the aforementioned composition. The present method is particularly suitable for treating or preventing overweight or obesity in humans.

Pectins

Pectins are carbohydrates generally obtained from dilute acid extracts of citrus or apple pulp. They, are also present in the cellular walls of vegetables and fruits. Pectins are also found in root crops such as carrots and beetroot, as well as in tubers, such as potatoes. Pectins are chemically defined as partial methyl esters of polygalacturonic acids, whereof the molecular weight can reach 200,000.

Pectin is the methylated ester of polygalacturonic acid. It is commercially extracted from citrus peels, apple pomace and sugar beet pulp. A typical pectin molecule comprises 200 to 1000 galacturonic acid units connected in a linear chain.

Pectin is divided into two main categories: high methoxylated pectin (hereafter referred to as HM pectin), which are characterized by a degree of methoxylation above 50% and low methoxylated pectin (hereafter referred to as LM pectin) having a degree of methoxylation below 50%. As used herein, "degree of methoxylation" (also referred to as DE or "degree of esterification") is intended to mean the extent to which free carboxylic acid groups contained in the polygalacturonic acid chain have been esterified (e.g. by methylation).

The LM pectins are further subdivided into two groups: low methoxylated amidated, and low methoxylated conventional. As used herein the "degree of amidation" (DA) is intended to mean the extent to which ester groups contained in the polygalacturonic acid chain have been converted to amide groups by reaction with e.g. an ammonium hydroxide in solution.

The LM pectins as used in the present invention are characterized by a degree of methoxylation below 50%, preferably between 5% and 45%, more preferably between 10% and 40%, even more preferably between 15% and 35%. According to a further preferred embodiment, the LM pectins are amidated, the degree of amidation preferably being below 30%, preferably below 25%, even more preferably below 20%. The preferred lower limit of the degree of amidation is 5%, more preferably 10%.

The LM pectins in the composition according to the present invention are capable of forming a sufficiently rigid matrix at a pH as present in the stomach of a normal human, e.g. pH 3. It is therefore necessary to include at least 0.05 g LM pectin per 100 ml (0.05 wt %) of the composition according to the present invention, preferably at least 0.1 g LM pectin, more preferably at least 0.25 g, even more preferably at least 0.5 g, most preferably at least 0.65 g per 100 ml. However, LM pectin cannot be included unrestrictedly, since at high concentrations the composition will acquire an unacceptable high viscosity. Preferably the composition has a LM pectin content below 5 wt. %, more preferably below 1.5 wt. % even more preferably below 1 wt. %.

Alginate

Alginates are linear unbranched polymers containing –(1→4)-linked D-mannuronic acid and α-(1→4)-linked L-guluronic acid residues with a wide range of average molecular weights (100–100000 residues) to suit the application. Suitable sources of alginate include seaweeds and bacterial alginates. Preferably sodium alginate and potassium alginate are used as a source of alginate.

The alginate in the present composition should be capable of forming a sufficiently rigid matrix at a pH as present in the stomach of a normal human, e.g. pH 3. It is therefore necessary to include at least 0.05 g alginate per 100 ml (0.05 wt %) of the present composition, preferably at least 0.1 g per 100 ml, more preferably at least 0.25 g per 100 ml, even more preferably at least 0.4 g per 100 ml. However, alginate cannot be included unrestrictedly, since the composition will become unacceptably viscous. Preferably the present composition has an alginate content below 5 wt. %, more preferably below 2.5 wt. % even more preferably below 1 wt. %.

Calcium salt The composition according to the invention preferably contains a calcium salt, which is substantially less soluble in water at 20° C. and at the pH of the composition then at 37° C. and a pH below 5. Such a calcium salt, when present in the composition in an amount that exceeds its maximum solubility, will solubilise in the stomach under the influence of pH-reduction and/or temperature increase. Thus the calcium ion concentration in the composition will increase, which will automatically stimulate pectin and/or alginate gellation.

Because of the gellation inducing effect of calcium ions, the concentration of such ions in the present liquid composition (at near neutral pH) is preferably relatively low. The limited presence of (dissolved) calcium ions at around neutral pH prevents the formation of a gel matrix which would impart unacceptably high viscosity. Thus, in a preferred embodiment, the calcium salt(s) used in the present composition has a solubility below 0.15, more preferably below 0.1 gram, even more preferably below 0.06 gram per 100 ml (demineralised) water at 20° C. and pH 7. Preferably, the calcium salt(s) provide more than 0.2 gram dissolved calcium per 100 ml water at a pH below 5 and a temperature of 37° C., more preferably it provides more than 0.5 g/100 ml under these conditions. The calcium salt is preferably selected from the group consisting of calcium phosphate (e.g. tribasic, dibasic, monobasic or penta calcium triphosphate), calcium carbonate, calcium sulfate, calcium oxide, calcium citrate (e.g. mono calcium citrate or tri calcium citrate), a calcium salt coated with a substance which has limited solubility in water at pH 7 and is soluble at a pH below about 5 (hereafter referred to as coated calcium salts) and mixtures thereof. Examples of coatings and methods for the preparations of coated calcium salts are given in WO0038829, the entire content of which is hereby incorporated by reference. More preferably, the calcium salt is selected from the group consisting of coated calcium salt, calcium carbonate, calcium phosphate and mixtures thereof. Most preferable the majority of calcium salt is provided by calcium carbonate.

To provide optimal gelling characteristics, the composition according to the invention contains at least 1.25 mM calcium (equivalent to 5 mg Ca per 100 ml). Preferably the calcium concentration exceeds 2.5 mM (equivalent to 10 mg Ca/100 ml), more preferably it exceeds 5 mM, most preferably it exceeds 10 mM. Furthermore, the calcium concentration in the composition preferably does not exceed 1 M, more preferably it does not exceed 500 mM, even more preferably it does not exceed 100 mM. The calcium concentration in the composition may be determined by first completely solubilising the calcium, followed by the determination of the calcium concentration. The majority of the calcium will be present as a calcium complex and/or insoluble calcium salt when the composition is at neutral pH and thus unavailable to form a viscous matrix with the LM pectins. At a pH between 1 and 5, the calcium will mostly be solubilized from and/or present as a pectin-calcium complex.

In order to decrease unfavorable effects of the LM pectin containing composition on the calcium intestinal absorption, the composition preferably contains a concentration of calcium, which exceeds 0.5 times the concentration of negative charges provided by the LM pectin.

The concentration of negative charges can be calculated using the following formula;

$$\text{Concentration negative charges} = \frac{MW_g}{MW_g + (MW_e \times DE)} \times \frac{(100 - DE)}{100} \times C_p$$

MW$_p$=Molecular weight pectin (g/mol)
MW$_E$=Molecular weight galacturon unit (g/mol)=194 g/mol
MW$_e$=Molecular weight side chain (g/mol)=14 g/mol
DE=degree of esterification (%)
C$_p$=concentration pectin (g/l)
Oligosaccharide The term indigestible oligosaccharides as used in the present invention refers to saccharides which have a degree of polymerisation of monose units exceeding 2, more preferably exceeding 3, most preferably exceeding 4, which are not or only partially digested in the intestine by the action of acids or digestive enzymes present in the human upper digestive tract (small intestine and stomach) but which are fermented by the human intestinal flora.

The degree of polymerisation of the oligosaccharide is below 60 monose units, preferably below 40, even more preferably below 20, most preferably below 10.

The term monose units refers units having a closed ring structure, preferably hexose, e.g. the pyranose or furanose forms.

The oligosaccharide preferably comprises at least 90%, more preferably at least 95% monose units selected from the group consisting of mannose, arabinose, fructose, fucose, rhamnose, galactose, β-D-galactopyranose, ribose, glucose, galacturonic acid, glucuronic acid, xylose and derivatives thereof, calculated on the total number of monose units contained therein.

Suitable oligosaccharides are preferably fermented by the gut flora. The oligosaccharide used in the composition according to the present invention is preferably capable of significantly increasing the total cecal SCFA content. According to a preferred embodiment of the invention, the oligosaccharide, when administered in a sufficient amount, is capable of increasing total cecal SCFA content by at least 20%, compared to a composition wherein the oligosaccharide is absent, more preferably at least 50%, even more preferably at least 100%, most preferably at least 150%. The increase of total cecal SCFA content can be determined according to the method described by Campbell et al. (The Journal of Nutrition Vol. 127 No. 1 January 1997, pp. 130–136), the entire content of which is hereby incorporated by reference.

Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucopyranosly-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxo-hexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalcto-oligosaccharides (β-D-galactopyranosyl-(1-6)-[β-D-glucopyranosyl]$_n$-(1-4) α-D glucose), lactulose (4-O-β-D-glucopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactosel, II and III), fructans-Levan-type (β-D-((2→6)-fructofuranosyl)$_n$ α-D-glucopyranoside), fructans-Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, arabinooligosaccharides and mixtures thereof.

According to a further preferred embodiment the oligosaccharide is selected from the group consisting of fructans, fructooligosaccharides, indigestible dextrins galactooligosaccharides (including transgalactooligosaccharides), xylooligosaccharides, soybean oligosaccharides, arabinooligosaccharides and mixtures thereof.

The term fructans as used in this document can be divided in two classes, levan and inulin. Levans are β-2,6-linked fructans with variable degrees of β-2,1-linked side chains that are produced by a large variety of bacteria. Inulins and fructooligosaccharides on the on the other hand, are a group of linear glucosyl $\alpha(1\rightarrow2)(\text{fructosyl})_n\beta(2\rightarrow1)$fructose polymers with a degree of polymerisation (DP) ranging from 2 up to 60.

Fructooligosaccharides are produced, either by enzymatic hydrolysis of inulin or by transfructosylation of sucrose, If oligosaccharides have a DP lower than 9, they are named fructooligosaccharides. The main fructooligosaccharides are 1-kestose ($GF_1$), nystose ($GF_2$) and fructosylnystose ($GF_3$) (GF=glycosylfructo-oligosaccharide). The fructans components with a higher DP are named inulin.

Inulin is for example sold under the trademark Raftiline™ (Orafti Active Food Ingredients, Belgium). Fructooligosaccharides and oligofructose are for example sold under the trademark Raftilose™ (Orafti Active Food Ingredients, Belgium) and NutraFlora™ (Golden Technologies Company)

NutraFlora has been described to increase total cecal SCFA content by about 260%, Raftilose has been described to increase total cecal SCFA content by about 244%, (Campbell et al: The Journal of Nutrition Vol, 127 No. 1 January 1997, pp. 130–136). Hydrolyzed inulin is available from Rhone-Poulenc, Inc, Cranbury, N.J.

The term galacto-oligosaccharides (including transgalactooligosaccharides) refers to non-digestible carbohydrates structured as chains rich in galactose with mostly a glucose end-unit. Two types of galactooligosaccharides are distinguished. The galactooligosaccharides can be produced from lactose by the transglycosylating activity of β-galactosidase, β-galacto-oligosaccharides consist of a number of β-1,6-linked galactosyl residues linked to a terminal glucose unit via an β1,4-bond. Another type of galactooligosaccharides is isolated from soybeans. These α-galacto-oligosaccharides (galactosyl-sucrose oligosaccharides) include raffinose, stachyose and verbascose and consist of galactose residues linked α-1,6 to the glucose moiety of sucrose. The physiological effects of these oligosaccharides appear to be similar to the β-linked galactose oligomers. The composition of galactooligosaccharides may vary in chain length and type of linkage between the monomer units.

Transgalactooligosaccharides are for example sold under the trademark Elix'or™ (Borculo Domo Ingredients, Netherlands). Galactooligosaccharides are available from Solabia, Pantin Cedex, France.

Indigestible dextrin, which is produced by pyrolysis of corn starch, comprises $\alpha(1\rightarrow4)$ and $\alpha(1\rightarrow6)$ glucosidic bonds, as are present in the native starch, and contains $1\rightarrow2$ and $1\rightarrow3$ linkages and levoglucosan. Due to these structural characteristics, indigestible dextrin contains well-developed, branched particles that are partially hydrolysed by human digestive enzymes.

Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

The oligosaccharides are preferably included in the composition according to the invention in an amount exceeding 0.1 wt. %, preferably exceeding 0.2 wt. %, more preferably exceeding 0.5 wt. % and even more preferably exceeding 0.9 wt. %. Although the administration of considerable amounts of oligosaccharides will generally not lead to undesirable side effects, the present composition preferably has an oligosaccharide content below 20 wt. %, more preferably below 10 wt. % even more preferably below 5 wt. %.

It is important to recognize that the amount of LM pectins administered to the subject will determine the required amount of oligosaccharides present in the composition according to the invention. Preferably the weight ratio oligosaccharides to pectins exceeds 0.25, more preferably is between 0.5 and 100, even more preferably between 0.75 and 50, most preferably between 1 and 5.

Water

Water is of great importance for the prevention of body weight increase and/or reducing obesity. The present composition preferably contains between 50 and 99 wt. % water, more preferably between 60 and 95 wt. %, even more preferably between 75 and 90 wt. %.

Supplementary Components

The composition according to the invention can suitably be used to replace one or more meals or snacks during the day. The composition preferably contains additional nutritional ingredients, which further contribute to a healthy diet.

Bioactive Agents

Vitamins are preferably added to the composition according to the invention. The vitamins added may suitably be selected from the group consisting of Vitamin A, Vitamin E, Vitamin K, Vitamin C, Vitamin D, Thiamin, Riboflavin, Niacin, Vitamin B6, Folic acid, Vitamin B12, Biotin, Pantothenic acid and mixtures thereof. Preferably the composition contains at least 3 specified bioactive agents selected from this group. According to a preferred embodiment, at least vitamin D is present in the composition to further aid the calcium absorption. Obese or overweight subjects often suffer from vitamin D deficiency.

The easiest and most natural way to get Vitamin D is from exposure to sunlight, which causes the body to manufacture its own. However, humans wishing to reduce body weight often have a low self-esteem, and are therefore hesitant to expose themselves to sunlight, e.g. by sunbathing. Furthermore, common sources of vitamin D, such as dairy product like milk are often replaced by soda drinks in the diets of overweight subjects. The bioactive agents may be present in the composition according to the invention in an amount ranging from 5% of the recommended daily intake (RDA) to 250% of the RDA of the specific bioactive agents. The RDA has been published by the U.S. Food and Drug Administration.

Minerals

Minerals may be added to the present composition. The minerals added may suitably be selected for the group consisting of iron, zinc, copper, chromium, iodine, selenium, magnesium, manganese, molybdenum, choline, potassium, phosphate, chloride and mixtures thereof and preferably contains at least 3 specified minerals selected form this group.

The minerals are preferably present in the composition according to the invention in an amount ranging from 5% of the recommended daily intake (RDA) to 250%, preferably between 10 and 50% of the RDA of the specific minerals. The RDA has been published by the U.S. Food and Drug Administration.

Fibers

The composition preferably includes one or more additional fibers other than LM pectins or non-digestible oligosaccharide having a degree of polymerisation between 2 and 60. The additional fiber may be selected from the group of soluble and insoluble fibers. The fiber may further stimulate the satiety effect of LM pectins by decreasing the rate of stomach emptying and/or provide a slow release of sugars in the intestine which also contributes to an extended feeling of satiety. Furthermore, the fibers may prevent or decrease constipation and further contribute to a blood serum cholesterol lowering effect of the composition according to the present invention.

When the additional fibre is soluble fibre, the soluble fibre of the present invention is preferably selected from the group consisting of high methoxylated pectin, chitosan, -glucan, soluble fibre from psyllium husk (hereafter referred to as psyllium), xanthan gum, guar gum, locust bean gum, gum arabic, soy fibre and mixtures thereof, more preferably from the group consisting of psyllium, pectin, -glucan or mixtures thereof. The -glucan is preferably obtained from whole oat, and even more preferably is part of a whole oat soluble fiber composition.

Preferably the additional fiber is included in the composition in an amount between 0.1 g and 10 gram fiber per 100 ml, more preferably between 0.2 and 5 gram, which preferably includes between 0.05 and 2 gram -glucan per 100 ml.

Proteins

Proteins are essential in human nutrition. The composition according to the invention therefore preferably includes between 1 and 20 grams protein per 100 ml of the composition, more preferably between 2 and 10 grams.

The protein is preferably obtained from a vegetable source, more preferably includes at least about 1 gram soy protein per 100 ml, wherein the soy protein is preferably selected from soy protein concentrate and soy protein isolate.

Digestible Carbohydrates

The composition may contain digestible carbohydrates. When the composition is designed to replace one or more meals, it is desirable to include digestible carbohydrates. The term carbohydrates includes digestible polysaccharides and monosaccharides, i.e. carbohydrates which are digested by the intestinal acids and/or intestinal enzymes and/or are absorbed by the intestinal cells. The digestible carbohydrate may for example be a starch, a maltodextrin or a monosaccharide. Preferably the composition includes 0.2 to 5 wt. % monosaccharide, even more preferably between 1 and 3 wt. %. According to a further preferred embodiment the monosaccharide mainly consists of fructose.

The inclusion of digestible polysaccharides such as starches and maltodextrins in the present composition may further contribute to the feeling of satiety. When the composition is in a ready-to-drink form, the composition preferably has a low (non-maltodextrin) starch content because inclusion of an appreciable amount of starch will inevitably lead to a strong viscosity increase during heat processing (e.g, sterilization). Hence, preferably the composition contains below 1 gram starch per 100 ml, more preferably below 0.5 gram, even more preferably below 0.2 grams. Digestible maltodextrins (DE between 5 and 30, preferably around 20) are advantageously added to the present composition to provide a satiety effect as maltodextrins, in contrast to other starch and starch derivatives, can suitably be used in heat processed liquids. Preferably, the present composition preparation contains between 0.5 and 20 g maltodextrins per 100 ml, even more preferably between 2 and 10 grams maltodextrins per 100 ml.

Fat

When the composition is aimed to replace one or more meals, it is desirable to include lipids or fat. Preferably the lipids are obtained from plant sources, e.g. canola oil or olive oil, which have a relatively high content of monounsaturated and/or polyunsaturated fatty acids. Preferably at least about 10 wt. % of the lipids included in the product are polyunsaturated fatty acids. The content of lipids included in the composition is preferably between 0.2 and 10 wt. %, more preferably between 0.5 and 5 wt. %.

Application

A consumer may prepare the present composition from e.g. a powder that contains the pectin and/or alginate, calcium and oligosaccharide by simply adding a predetermined amount of water. The present composition may also be in a ready-to-drink form, which can be consumed without the need for further preparation, i.e. does not require the addition of water before ingestion.

According to a preferred embodiment, the present composition is provided as a packaged beverage product comprising at least 25 ml, more preferably at least 50 ml, even more preferably at least 100 ml of the composition. Preferably the contents of the packaged beverage product do not exceed 2000 ml, more preferably the contents are below 1000 ml, even more preferably below 500 ml, most preferably below 400 ml.

When the present composition is supplied in powder form it is preferably accompanied with a instruction to reconstitute the powder in a predetermined volume of water, for example by shaking or blending, to obtain the composition according to the present invention. Preferably the composition is consumed within about 60 minutes after reconstitution.

The liquid edible composition is preferably sterilized or pasteurized prior to consumption. Furthermore the present composition preferably contains one or more flavorings and/or colorants.

The composition is preferably used to replace one or more meals, preferably one or more meals selected from breakfast, lunch or dinner. Preferably the composition is consumed more than one time per day.

Whenever the term dose or dosage is used within this document, this refers to the total consumption of the present composition within a fairly narrow time span. Whenever reference is made to a certain quantity that is administered per dose or dosage, said quantity is preferably administered within one hour, more preferably within 30 minutes, even more preferably within 10 minutes.

Viscosity

The present liquid composition has a viscosity below 600 mPas at a shear rate of $100s^{-1}$ at 20° C. and a viscosity of at least 125% of said viscosity at a pH below 5 and a temperature of 37° C.

The liquid edible composition preferably has a limited viscosity. Therefore, according to a preferred embodiment the present composition has a viscosity below 250 mPas, more preferably below 100 mPas, most preferably below 50 mPas at a shear rate of $100s^{-1}$ at 20° C.

Preferably, at pH 3 and 37° C. the composition has a viscosity which is at least 150% of the aforementioned viscosity at near neutral pH, more preferably above 200%, even more preferably above 400%. Preferably the composition has a viscosity at pH 3 and 37° C. which exceeds 250 mPas, more preferably exceeds 300 mPas, most preferably exceeds 400 mPas.

Whenever the term viscosity used in the present document, this refers to the physical parameter which is determined according to the following method:

The viscosity may be determined using a Carri-Med CSL rheometer. The used geometry is of conical shape (6 cm 2 deg acrylic cone) and the gap between plate and geometry is set on 55 $\mu$m. A linear continuous ramp shear rate is used from 0 to 150 $s^{-1}$ in 20 seconds. The rheometer's thermostat is set on the appropriate temperature (e.g. 20° C. or 37° C.).

In order to determine the viscosity at acidic pH (pH 3), first a sufficient amount of 1 M HCl is homogeneously admixed (drop-wise under very gentle stirring for about 20 sec, to prevent the breakdown of the gel) to the liquid composition to adjust the pH of the composition to pH 3. Thereafter the composition is left standing at 20° C. for about 10 minutes. Subsequently the composition thus obtained is used to determine the viscosity at pH 3, according to the method described above.

To decrease the viscosity of the present composition (at near neutral pH), ingredients may advantageously be added that are selected from the group of polyols, e.g. sorbitol, maltitol, or erytritol. These ingredients offer the advantage that they hardly affect the viscosity of the present composition at low pH. Preferably these viscosity decreasing ingredients are added in an amount of 0.5 to 50 wt. %. Suitable examples of the use of polyols in the present preparation are given in WO0038829, the entire content of which is hereby incorporated by reference.

According to another embodiment of the invention the present composition may additionally comprise an anion which forms a complex or insoluble salt with calcium at pH 7. Exemplary and preferably the anion is provided by a salt that is soluble at pH 7. The salt may be a potassium or sodium salt of citrate or phosphate. Preferably such salt is used in an amount between 0.2 and 10 wt. %.

EXAMPLES

Example 1

A composition is prepared comprising:

0.55 gram 31% methoxylated, 17% amidated apple pectin
154 mg calcium carbonate
0.4 g tri potassium citrate
1 gram Fibersol 2™ (Matsutani Chemical industry Co., Japan)
Filled up with water to 100 ml (pH adjusted to 7 with 10% KOH solution)

At pH 7 the composition has a viscosity of 32 mPas at a shear rate of $100s^{-1}$, 20° C. At pH 3, 37° C. a rigid gel is formed. (viscosity >>1000 mPas)

Example 2

A composition is prepared comprising:

0.62 gram 31% methoxylated, 17% amidated apple pectin
154 mg calcium carbonate
0.4 g tri potassium citrate
1 gram Fibersol 2™ (Matsutani Chemical industry Co., Japan)
4.55 gram soy protein isolate
0.86 gram oat bran
3.18 gram maltodextrin 19 DE
1.54 gram fructose
0.31 gram canola oil
0.31 gram olive oil
80 mg vitamin blend
60 mg minerals and trace element blend
Filled up with water to 100 ml pH adjusted to 7 with 10% KOH solution)

This composition is homogenized and sterilized. At pH 7 and 20° C. the composition has a viscosity of 27 mPas at a shear rate of $100s^{-1}$. At pH 3 and 37° C. the composition has a viscosity of 150 mPas at a shear rate of $100s^{-1}$.

Example 3

A composition comprising:

0.1 gram 31% methoxylated, 17% amidated apple pectin
50 mg calcium carbonate
0.4 g tri potassium citrate
1 gram Fibersol 2™ (Matsutani Chemical industry Co., Japan)
0.5 gram sucrose
5 gram full cream milk powder
11 gram oat bran
Filled up with water to 100 ml (pH adjusted to 7 with 10% KOH solution)

At pH 7 the composition has a viscosity of 48 mPas at a shear rate of $100s^{-1}$. At pH 3 a rigid gel is formed (viscosity >>1000 mPas).

What is claimed is:

1. A liquid edible composition with a pH of more than 6, a viscosity below 600 mPas at a shear rate of $100\ s^{-1}$ and 20° C., and a viscosity of at least 125% of the aforementioned viscosity at a pH below 5 and a temperature of 37° C., the composition comprising:
   a. at least 0.05 wt. % of pectin having a degree of methoxylation below 50% and/or of alginate;
   b. at least 5 mg calcium per 100 ml wherein the calcium is provided by a calcium salt which has a solubility below 0.15 grams per 100 ml demineralized water at 20° C. and pH 7; and
   c. at least 0.1 wt. % indigestible oligosaccharide having a degree of polymerisation exceeding 2 and below 60.

2. A composition according to claim 1, comprising between 0.4 and 5 wt. % pectin having a degree of methoxylation between 5% and 45%.

3. A composition according to claim 1, wherein the calcium is provided by a calcium salt which has a solubility below 0.10 grams per 100 ml (demineralized) water at pH 7 and 20° C.

4. A composition according to claim 1, comprising between 0.1 and 10 wt. % indigestible oligosaccharide having a degree of Polymerisation above 2 and between 2 and 40.

5. A composition according to claim 1, comprising between 0.1 and 10 grams calcium per 100 ml.

6. A composition according to claim 1, wherein the composition is sterilized or pasteurized and/or contains added flavoring.

7. A composition according to claim 1, wherein the oligosaccharide is selected from the group consisting of fructans, fructooligosaccharides, indigestible dextrins galactooligosaccharides, xylooligosaccharides, soybean oligosaccharides, arabinooligosaccharides and mixtures thereof.

8. A composition according to claim 1, wherein the calcium salt is selected from the group consisting of calcium phosphate, calcium carbonate, calcium sulfate, calcium oxide, calcium citrate, a calcium salt coated with a substance which has limited solubility in water at pH 7 and which is soluble at a pH below 5 and mixtures thereof.

9. A composition according to claim 1, comprising between 50 and 98 wt. % water.

10. A composition according to claim 1, comprising between 1 and 25 grams protein per 100 ml.

11. A composition according to claim 1, comprising between 0.2 and 10 wt. % fat.

12. A packaged beverage product comprising between 50 and 1000 ml of a composition according to claim 1.

* * * * *